United States Patent [19]

Malzahn

[11] 4,450,047
[45] May 22, 1984

[54] PROCESS FOR RECOVERING ANHYDROUS ALKANESULFONIC ACIDS BY REDUCED PRESSURE, FALLING FILM EVAPORATION

[75] Inventor: Dale E. Malzahn, Dearborn Heights, Mich.

[73] Assignee: Penwalt Corporation, Philadelphia, Pa.

[21] Appl. No.: 461,776

[22] Filed: Jan. 28, 1983

[51] Int. Cl.³ .............. B01D 3/10; B01D 1/22; C07C 143/02

[52] U.S. Cl. ...................... 203/15; 203/73; 203/89; 203/72; 203/90; 203/91; 159/48.2; 159/49; 202/172; 260/513 R

[58] Field of Search ............... 260/513 R, 502 R, 400, 260/503; 203/15, 89, 14, 91, 90, 73, 72; 159/47.1, 48 L, 49, 13 R, 13 A, 13 B, 3; 202/172, 236

[56] References Cited

U.S. PATENT DOCUMENTS

| | | |
|---|---|---|
| 2,124,729 | 7/1938 | Castner et al. .................... 23/306 |
| 2,234,166 | 3/1941 | Hickman ........................... 202/236 |
| 2,285,337 | 6/1942 | Kapp et al. ......................... 203/15 |
| 2,711,388 | 6/1955 | Mottern et al. .................... 203/15 |
| 2,728,717 | 12/1955 | Madorsky ......................... 202/173 |
| 2,909,469 | 10/1959 | Griffith ............................. 202/172 |
| 3,003,930 | 10/1961 | Pugh et al. ....................... 202/236 |
| 3,444,049 | 5/1969 | Starmer et al. .................. 202/172 |
| 3,509,206 | 4/1970 | Nielsen .......................... 260/502 R |
| 3,684,459 | 8/1972 | Tate et al. ........................ 422/138 |
| 3,713,786 | 1/1973 | Umstead ........................... 23/307 |
| 3,820,582 | 6/1974 | Rönnholm ......................... 159/18 |
| 4,035,242 | 7/1977 | Brandt ............................... 203/15 |
| 4,164,441 | 8/1979 | Kühnlein et al. ................ 159/13 A |
| 4,173,246 | 11/1979 | Nunlist et al. .................... 159/6 W |
| 4,289,577 | 9/1981 | Mabuchi et al. .................... 159/5 |

Primary Examiner—Wilbur L. Bascomb, Jr.

[57] ABSTRACT

Water is removed from methanesulfonic acid to produce an anhydrous product of high purity by spraying wet methanesulfonic acid (MSA) onto the walls of a vertical, heated tube which is maintained at reduced pressure. The water evaporates as the acid flows down the walls of the tube and dry MSA is removed at the bottom.

12 Claims, 3 Drawing Figures

PROCESS FOR RECOVERING ANHYDROUS ALKANESULFONIC ACIDS BY REDUCED PRESSURE, FALLING FILM EVAPORATION

BACKGROUND OF THE INVENTION

In the manufacture of methanesulfonic acid, an aqueous product which normally contains about 20 to 35 weight percent of water is produced. In order to obtain an anhydrous, (<2 wt. percent water) product, useful, for example, as a reaction medium in the preparation of aromatic peroxy acids where excess water retards the reaction, the water must be removed while minimizing the formation of decomposition products. Of special concern is the need to avoid the formation of methyl methanesulfonate ($CH_3SO_2OCH_3$). This compound is a known carcinogen. A two-step distillative purification process for lower-alkanesulfonic acids is disclosed in U.S. Pat. No. 4,035,242. Water vapor is removed in the first step by distillation and the major portion of the alkanesulfonic acid is vaporized and removed by vacuum distillation in the second step. In the example, a product having a purity of 98.89 weight percent is obtained. Besides water, the product is reported to contain an average of 0.08 weight percent methyl methanesulfonate and 0.46 weight percent sulfuric acid. I have now found a process in which an anhydrous alkanesulfonic acid can be prepared, in a single step, without vaporizing the the acid product, to a purity of at least 99.5 weight percent. The acid contains less than 1.0 ppm of methyl methanesulfonate and no detectable sulfates.

BRIEF SUMMARY OF THE INVENTION

In accordance with this invention, there is provided a process for reducing the water content of a lower-alkane-sulfonic acid while minimizing the formation of decomposition products. A mixture containing water and lower-alkane-sulfonic acid is placed onto the internal surface of a vertical evaporator column to form a film of the mixture on the surface. The surface is heated and the column is maintained at subatmospheric pressure so that the water evaporates as the mixture flows by gravity down the surface of the column. Water vapor is removed from the top of the column and the lower-alkanesulfonic acid, having a reduced water content, is removed from the bottom of the column.

The column can be constructed of several sections having different internal diameters to provide a progressively larger internal volume from bottom to top so as to facilitate the evaporation and removal of the larger water vapor stream in the upper portion of the column. Two or more columns can be arranged in parallel to provide increased throughput.

DETAILED DESCRIPTION

Figure 1:
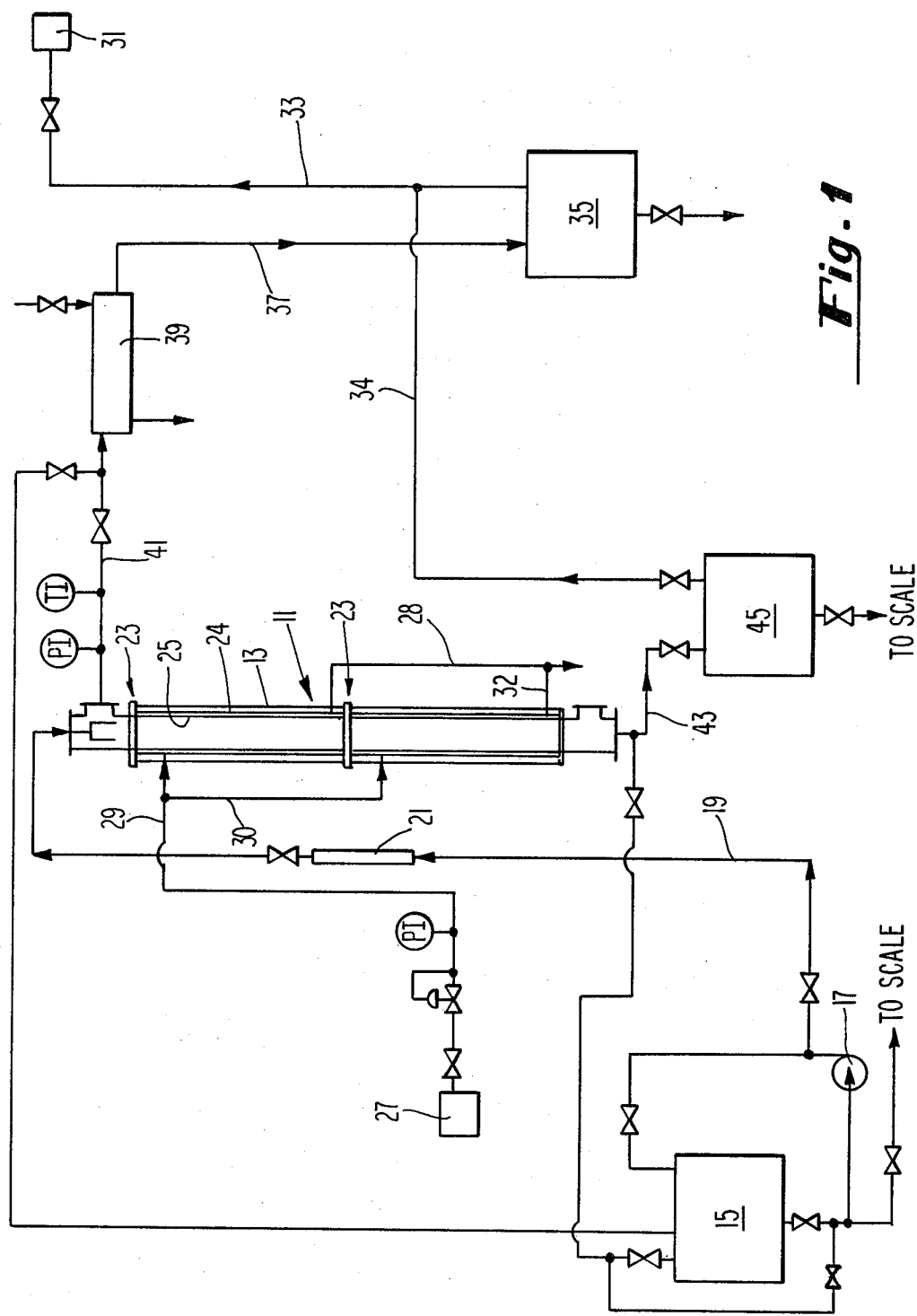
FIG. 1 is a schematic diagram illustrating a system for carrying out the process of the inventions.

Turning now to FIG. 1, a vertically-arranged, steam-jacketed falling film evaporator column 11 is constructed of a 2-inch in diameter, 11-foot long section of jacketed, glass-lined steel pipe 13. Storage tank 15 is provided for the aqueous alkanesulfonic acid. Pump 17 is provided to feed the alkanesulfonic acid from storage tank 15 through line 19 to the top of column 11 onto a TEFLON ® distributor plate 23. Rotameter 21 monitors the flow of aqueous acid to column 11. Plates 23 act to form and maintain a film of the aqueous acid on the surface 25 of inner wall 24 of pipe 13. Wall 24 is heated to temperatures of from about 300° to 375° F. by steam under pressure, or by other suitable means, fed from a supply 27, through lines 29 and 30 to the jacket portion of pipe 13. The steam leaves the jacket through lines 28 and 32. Line 41 is provided to remove water vapor and some acid which is also vaporized to a cold water condenser 39. Weak acid recovery tank 35 is used to collect the condensed water-acid mixture from line 37. Product tank 45 is provided to collect the anhydrous acid. The central core of pipe 13 is arranged to be maintained at a reduced pressure of from about 15 to 50 mm of Hg absolute by a two-stage steam jet vacuum system 31 which is connected to the inner core of pipe 13 and also to weak acid recovery tank 35 and product tank 45 through lines 33 and 34 so as to equalize the pressure in the system.

In operation, an acid-water mixture, for example 70 weight percent methanesulfonic acid (MSA) and 30 weight percent water, at ambient temperature in storage tank 15 is fed by pump 17 through line 19 and rotameter 21 at the rate of about 17 pounds per hour to the top of column 11 where it is placed onto distributor plate 23 which forms a film of aqueous acid on surface 25 of wall 24. Wall 24 is heated by steam (10 lbs/hour) to a temperature of about 375° F. The film flows by gravity down the surface 25. The central core of pipe 13 is maintained at a reduced pressure of about 25 mm of mercury absolute so that the water is removed from the aqueous acid film efficiently without either vaporizing excessive amounts of MSA or requiring heating of the MSA to a temperature which would cause significant decomposition. The water and some vaporized MSA (overhead) leaves column 11 at the top through line 41 which carries the vapor to cold water condenser 39. The condensed liquid is removed to weak acid recovery tank 35 from which the acid-water mixture, which contains, for example, about 75% water and 25% MSA, is returned to the MSA production process. A highly purified (>99.5 wt. %), substantially anhydrous (<0.5 wt. % water), MSA product is recovered at the bottom of column 11 through line 43 and is collected in product tank 45.

Figure 2:
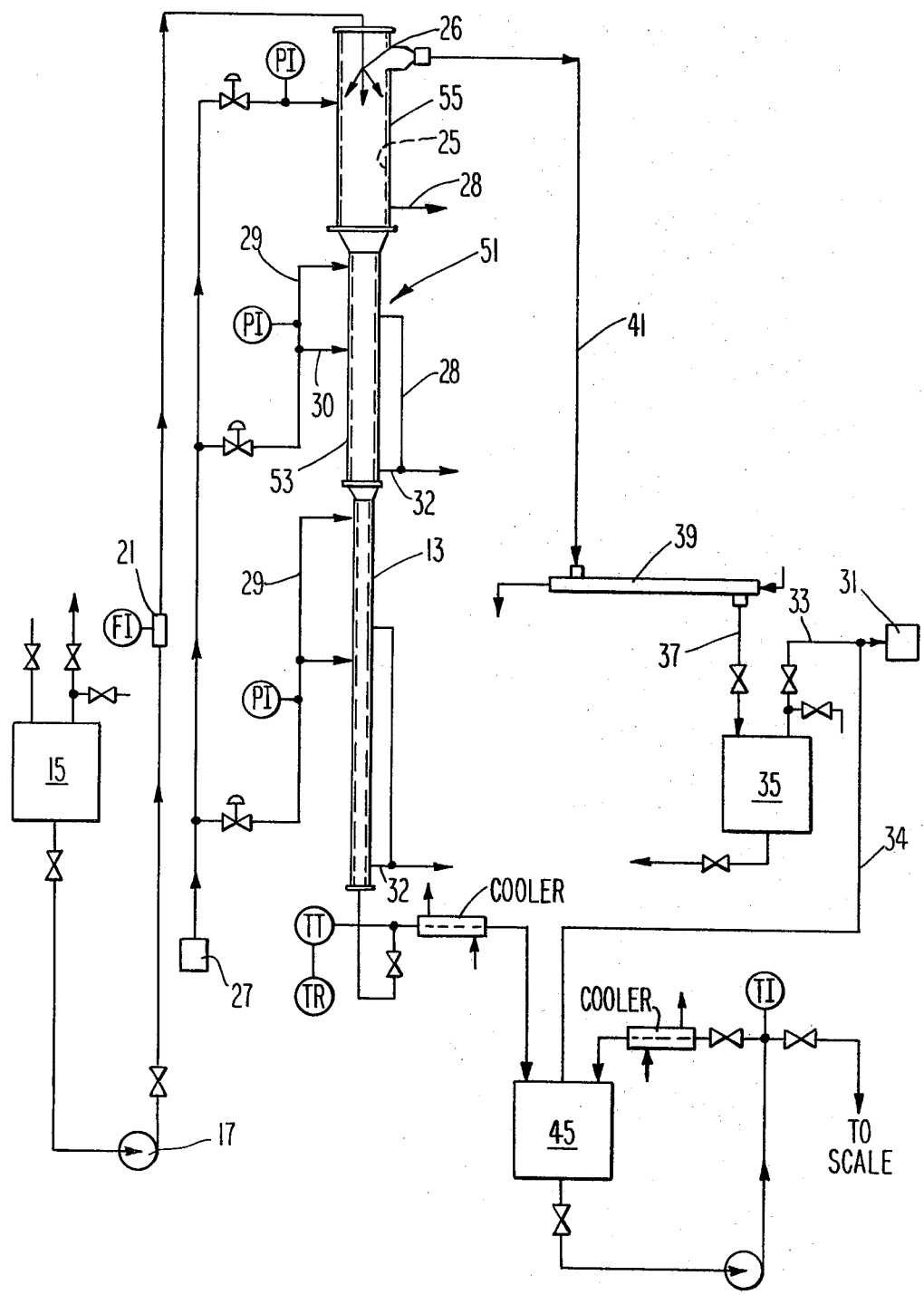
FIG. 2 is a schematic diagram illustrating an alternate system for carrying out the process of the invention in which the evaporation column is formed of several sections of different internal diameters.

FIG. 2 illustrates an apparatus for carrying out the process of the invention with an evaporator column 51 having three sections, 13, 53 and 55 of jacketed steel pipe. Section 55 is an 8-inch in diameter, 6-foot long, jacketed, glass-lined pipe, and section 53 is a 4-inch in diameter, 10-foot long, jacketed, glass lined pipe. Pipe 13 is 2 inches in diameter and 11 feet long as described in FIG. 1. A steam system is provided so that the steam is supplied at a different pressure to the jacket of each evaporator section because of the pressure rating limitations of the jacketed glass-lined pipe. For example, the following steam pressures, feed rates, and temperatures are employed:

TABLE I

| Section | Rate lbs/hr | Steam PSIG | Temperature °C. |
|---|---|---|---|
| Top | 40 | 60 | 153° |
| Middle | 34 | 125 | 178° |
| Bottom | 20 | 175 | 192° |

The remainder of the apparatus is similar to that illustrated in FIG. 1 and corresponding parts are designated by the same reference numbers. A spray nozzle 26 is employed to spray the aqueous MSA onto the surface 25 at the top of section 55 to form the film on the surface in place of a distributor plate.

In Tables II and III, flow rates, in pounds per 24 hour day, for a typical operation of the process using the apparatus of FIG. 2 are given, along with the weight percent recovery of product. The temperatures and pressures are given in Table III. The walls of column 51 are heated to a temperature of about 300° F. in the top section, 325°-350° F. in the center section, and about 375° in the bottom section.

TABLE II

| Component | Feed lbs/day | Overhead lbs/day | Product lbs/day | Prod/Feed Wt. % Recovery |
|---|---|---|---|---|
| MSA | 869 | 123 | 746 | 86 |
| $H_2O$ | 373 | 369 | 3.8 | 1 |
| Total | 1242 | 492 | 750 | 60 |

TABLE III

| | Feed | Overhead | Product |
|---|---|---|---|
| Wt. % MSA | 70 | 25 | 99.5 |
| Temp. °C. | ambient | — | 130-140° |
| Pressure, mm Hg. abs. | — | 49 | 49 |

The product from a typical run was analyzed, and no methyl methane sulfonate could be detected (<1.0 ppm). The MSA contained at least 99.5% by wt. MSA, no detectable sulfates, and some trace impurities which were not identified. The remainder of the product was water, i.e., about 0.5 weight percent. The product was slightly darkened by the heating (APHA 500), and a small amount of 70 wt. % hydrogen peroxide was added to provide improved color (APHA 60). For example, about 12 ounces by volume of 70% aqueous $H_2O_2$ per six hundred pounds of product.

Figure 3:
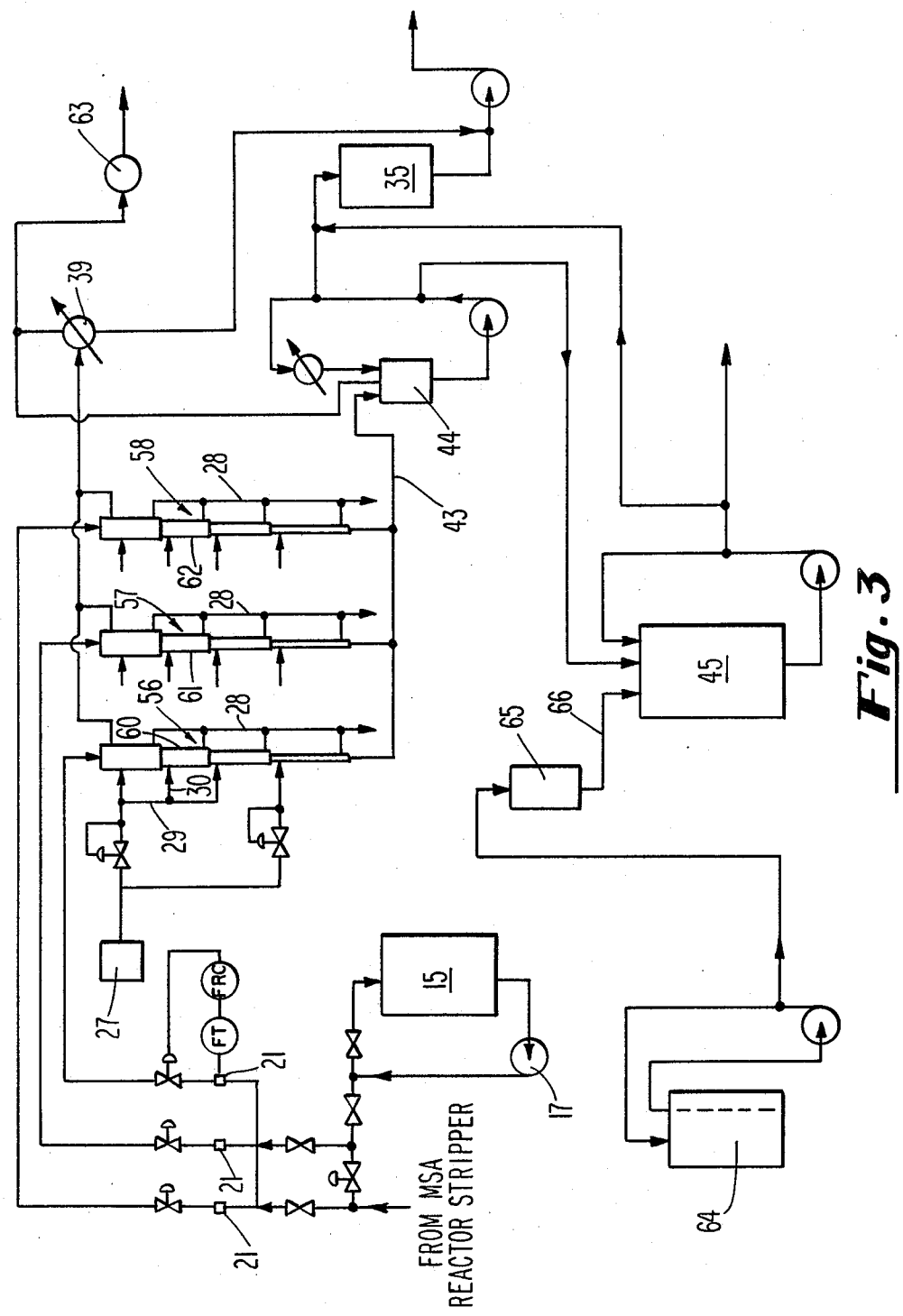
FIG. 3 is a schematic diagram illustrating an alternate system for carrying out the process of the invention in which a series of evaporator columns are arranged in parallel.

Turning now to the embodiment of FIG. 3, in order to provide increased throughput, three falling film evaporator columns 56, 57 and 58 are provided which each include four glass lined, steam jacketed sections with 6-inch in diameter sections 60, 61, 62 being added between the 4 and 8 inch sections of the column 51 shown in FIG. 2. Also, instead of a steam jet vacuum source, a vacuum pump 63 is employed to reduce the pressure in the evaporator columns to about 25 mm of Hg absolute. An intermediate hold tank 44 is provided whereby offspec product can be pumped to the weak acid recovery tank 35 for recycling to the reaction mixture. Supply 64 of 70% $H_2O_2$ is provided along with metering tank 65 so that small amounts of $H_2O_2$ can be added through line 66 to the product MSA order to improve the color. The remainder of the apparatus is similar to that shown in FIG. 2 and corresponding parts are shown by the same reference numerals.

Although the preferred embodiments of the process of the invention have been described with respect to the dehydration of MSA, it should be understood that the process can also be employed with water containing mixtures (5-60 percent by weight of water) of other lower-alkane sulfonic acids (i.e., 1-8 carbon atoms) such as ethanesulfonic acid by the proper selection of operating temperatures and pressures. The process provides substantially anhydrous alkanesulfonic acids, i.e., less than 0.5 weight percent water from materials containing upwards of 10% of water in a single evaporation step in which 85% by wt. or more of the acid in the feed stream is recovered in highly pure form. The product acid does not contain detectable amounts of carcenogenic byproducts.

I claim:

1. A process for reducing the water content of a lower-alkanesulfonic acid comprising placing a mixture containing water and said lower-alkanesulfonic acid onto the internal surface of an evaporator column so as to form a falling film of said mixture on said surface, operating said column at subatmospheric pressure and heating said surface so that water is vaporized from said mixture as said film flows down said surface, removing water vapor at the top of said column, and removing lower-alkanesulfonic acid having a water content of less than 2 percent and no detectable amounts of carcinogenic decomposition products at the bottom of said column.

2. The process of claim 1 wherein said mixture contains from about 5 to 60 percent by weight of water.

3. The process of claim 1 wherein the internal surface of the evaporator column is heated to a temperature of from about 300° to 375° F.

4. The process of claim 3 wherein the internal surface of the column is heated to a higher temperature at the bottom than at the top of the column.

5. The process of claim 1 wherein the column is operated at a pressure of from about 15 to 50 mm of Hg absolute.

6. The process of claim 1 wherein the evaporator column is provided with a larger internal diameter at the top so as to provide a larger volume of water vapor in the upper portion of the column.

7. The process of claim 6 wherein the evaporator column is formed in sections having different diameters so as to provide a progressively increasing volume of water vapor from the bottom to the top of the column.

8. The process of claim 7 wherein the diameter of the water vapor stream at the top section of the evaporator is 8" and the diameter of the water vapor stream at the bottom section of the evaporator is about 2".

9. The process of claim 1 wherein portions of said mixture are fed simultaneously to a plurality of evaporator columns which are arranged in parallel.

10. The process of claim 1 wherein said mixture comprises aqueous methanesulfonic acid.

11. The process of claim 10 wherein the lower-alkane-sulfonic acid is methanesulfonic acid and the product contains at least about 99.5% by wt. of methanesulfonic acid and less and 1 ppm of methyl methanesulfonate.

12. The process of claim 1 wherein said film is formed by spraying the mixture onto said surface.

* * * * *